United States Patent [19]

Duncan, Jr. et al.

[11] 4,032,642
[45] June 28, 1977

[54] 1-SUBSTITUTED-4-BENZYLPIPERIDINES

[75] Inventors: Robert Louis Duncan, Jr.; Robert Frederick Boswell, Jr., both of Richmond, Va.

[73] Assignee: A. H. Robins Company, Incorporated, Richmond, Va.

[22] Filed: Jan. 27, 1976

[21] Appl. No.: 652,683

Related U.S. Application Data

[62] Division of Ser. No. 531,832, Dec. 11, 1974, Pat. No. 3,956,296.

[52] U.S. Cl. ............................................. 424/267
[51] Int. Cl.² ......................................... A61K 31/445
[58] Field of Search ................................. 424/267

[56] References Cited

UNITED STATES PATENTS

| | | | |
|---|---|---|---|
| 2,739,968 | 3/1956 | Sperber et al. | 260/293.8 |
| 2,739,969 | 3/1956 | Sperber et al. | 260/293.8 |
| 3,000,896 | 9/1961 | Hoffmann et al. | 260/293.77 |
| 3,073,835 | 1/1963 | Rorig | 260/293.76 |
| 3,576,810 | 4/1971 | Duncan et al. | 260/293.74 |
| 3,806,526 | 4/1974 | Carr et al. | 260/293.84 |

*Primary Examiner*—Stanley J. Friedman

[57] ABSTRACT

Novel 1-substituted-4-benzylpiperidines having α-substituents on the 4-benzyl moiety useful as anti-inflammatory agents, sedatives, and tranquilizers are represented by the formula

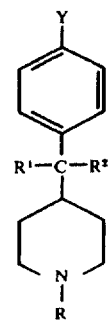

wherein R represents acetyl, aryloxyloweralkyl, aroylloweralkylcarbamoyl, N-lower-alkylcarbamoyl, N,N-dilower-alkylcarbamoyl, N-arylcarbamoyl, N-(ω-nitrogen containing heterocycle)lower-alkylcarbamoyl, N(-ω-aminolower-alkyl)carbamoyl, 2-hydroxy-3-(o-methoxyphenoxy)propyloxycarbonyl, 2-carbamoylethyl, or 4-(p-fluorobenzoyl)piperidinoethyl; $R^1$ represents hydrogen or hydroxy; $R^2$ represents phenyl, p-fluorophenyl, m-trifluoromethylphenyl or cyclohexyl; Y represents hydrogen or fluorine with the proviso that when Y is hydrogen and $R^2$ is phenyl, R is other than aroylloweralkyl. The pharmaceutically acceptable acid addition salts of the basic compounds of Formula I are included as part of the invention.

34 Claims, No Drawings

1-SUBSTITUTED-4-BENZYLPIPERIDINES

This application is a divisional application of copending application Ser. No. 531,832 filed Dec. 11, 1974, now U.S. Pat. No. 3,956,296.

FIELD OF INVENTION

The present invention relates to certain novel heterocyclic compounds which may be referred to as 1,4-disubstituted piperidines and is more particularly concerned with 1-substituted-4-($\alpha$-substituted) benzylpiperidines and 1-substituted-4-($\alpha,\alpha$-disubstituted) benzylpiperidines which are useful as antiinflammatory agents, sedatives and tranquilizers, compositions containing the same as active ingredients, and the methods of making and using them.

U.S. Pat. No. 3,806,526 discloses 1-aroylalkyl-4-diphenylmethylpiperidines having antihistaminic, antiallergenic, and bronchodilator activity. Great Britain Pat. No. 1,142,030 discloses optically active substituted piperidine compounds having antisecretory and central nervous system stimulating activity.

SUMMARY OF INVENTION

The invention is particularly concerned with 1-substituted-4-($\alpha,\alpha$-disubstituted) benzylpiperidines represented by the following general structural formula:

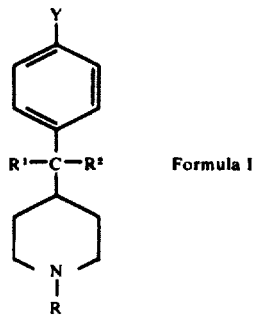

Formula I wherein;
R represents acetyl, aryloxyloweralkyl, aroylloweralkyl, carbomoyl, N-lower-alkylcarbomoyl, N,N-di-lower-alkylcarbamoyl, N-arylcarbamoyl, N-($\omega$-nitrogen containing heterocycle) lower-alkylcarbamoyl, N-($\omega$-aminoloweralkyl)carbamoyl, 2-hydroxy-3-(o-methoxyphenoxy)propyloxycarbonyl, 2-carbamoylethyl or 4-(p-fluorobenzoyl)-piperidinoethyl,
$R^1$ represents hydrogen or hydroxy,
$R^2$ represents phenyl, p-fluorophenyl, m-trifluoromethylphenyl, or cyclohexyl, and
Y represents hydrogen or fluorine with the proviso that when Y is hydrogen and $R^2$ is phenyl, R is other than aroylloweralkyl.

Included within the scope of the invention are the pharmaceutically acceptable acid addition salts of the basic compounds of Formula I.

DETAILED DESCRIPTION OF THE INVENTION

The anti-inflammatory activity was demonstrated in animals using a modification of the Evans Blue-Carrageenan Pleural Effusion Assay of Sancilio, L. F., which is described in the J. Pharmacol. Exp. Therap. 168, 199–204 (1969).

The tranquilizing properties were determined in mice using the Aggregated Mice Assay and the Conditioned Avoidance Behavior Assay as described by Johnson, D. N. et al., Arch. Int. Pharm. and Therap. 194(1), 197–208 (1971).

The sedative activity was demonstrated by gross observation of animals who had received compounds intraperitoneally and the antidepressant activity was demonstrated using the procedure of Englehardt et al., J. Med. Chem. 11(2)325 (1968).

It is therefore an object of the present invention to provide novel compounds and compositions possessing valuable pharmacological properties and a method for their preparation. Another object is to provide a novel method for the treatment of a living animal. Still another object is to provide compositions which possess beneficial activity and have minimum side effects. Additional objects will be apparent to one skilled in the art and still other objects will become apparent hereinafter.

In the definition of the symbols in the foregoing Formula I and where they appear elsewhere throughout this specification the terms have the following significance.

The term "lower alkyl" as used herein includes straight and branched chain radicals of up to eight carbon atoms inclusive, preferably no more than six carbon atoms, and is exemplified by such groups as methyl, ethyl, propyl, isopropyl, butyl, sec. butyl, tertiary butyl, amyl, isoamyl, hexyl, heptyl, octyl, and the like. A "lower-alkoxy" group has the formula -O-lower-alkyl.

The term "lower-alkylcarbamoyl" has the formula —C(O)N-(lower alkyl and the term "di-lower alkylcarbamoyl" has the formula —C(O)N-(lower alkyl)$_2$.

The term "N-($\omega$-nitrogen containing heterocycle) lower-alkylcarbamoyl" has the formula —C(O)NH-lower alkyl-heterocycle. The heterocyclic moiety includes morpholino, piperidino, pyridino, 2-(3- or 4-)pyridyl, 2-(or 3-)pyrrolidinyl or 2-(3- or 4-) piperidinyl but is not limited thereto.

An "aryl" radical refers to the phenyl radical or to a phenyl radical substituted by any radical or radicals which are not reactive or otherwise interfering under the conditions of reaction, such radicals including acetyl, lower alkoxy, lower alkyl, trifluoromethyl, chlorine, bromine, fluorine, and the like. The aryl radicals have preferably no more than one to three substituents such as those given above and, furthermore, these substituents can be in various available positions of the aryl nucleus and, when more than one substituent is present, can be the same or different and can be in various position combinations relative to each other.

An "aroylloweralkyl" radical has the formula aryl-C(O)-loweralkyl and includes such radicals as benzoylethyl, benzolylpropyl, halobenzoylethyl, halobenzoylpropyl, trifluoromethylbenzoylpropyl, lower-alkoxybenzoylpropyl, lower-alkylbenzoylpropyl and the like.

An "aryloxyloweralkyl" radical has the formula aryl-o-loweralkyl and includes such radicals as phenoxyethyl, phenoxypropyl, halophenoxypropyl, lower-alkoxyphenoxypropyl, halolower-alkoxyphenoxypropyl, acetyl-lower-alkoxyphenoxypropyl and the like.

This invention also includes pharmaceutically acceptable acid addition salts of the basic compounds of Formula I which salts are formed with nontoxic organic and inorganic acids. Such salts are conveniently prepared by methods known in the art. When the compounds are to be used as intermediates for preparing other compounds or for any other non-pharmaceutical use, the toxicity or nontoxicity of the salt is immaterial; when the compounds are to be used as pharmaceuticals, they are most conveniently used in the form of nontoxic acid-addition salts. Both toxic and nontoxic salts are therefore within the purview of the invention. The acids which can be used to prepare the preferred pharmaceutical acceptable acid addition salts are those which produce, when combined with the free bases, salts whose anions are relatively innocuous to the animal organism in therapeutic doses of the salts, so that beneficial physiological properties inherent in the free bases are not vitiated by side effects ascribable to the anions.

The base is reacted with the calculated amount of organic or inorganic acid in aqueous miscible solvent, such as ethanol or isopropanol, with isolation of the salt by concentrations and cooling, or the base is reacted with an excess of the acid in aqueous immiscible solvent, such as ethyl ether or isopropyl ether, with the desired salt separating directly. Exemplary of such organic salts are those formed with oxalic, maleic, fumaric, benzoic, ascorbic, pamoic, succinic, methanesulfonic, acetic, propionic, tartaric, citric, lactic, malic, citraconic, itaconic, hexamic, p-aminobenzoic, glutamic, stearic acid and the like. Exemplary of such inorganic salts are those formed with hydrochloric, hydrobromic, sulfuric, sulfamic, phosphoric and nitric acids.

The starting materials for the novel compounds of Formula I are 4-[α-(p-fluorophenyl)-α-hydroxyl-p-fluorobenzylpiperidine, 4-[α-(p-fluorophenyl)-benzyl]piperidine, 4-(α-phenyl-α-hydroxy)-p-fluorobenzyl-piperidine, 4-(α-phenyl)-p-fluorobenzylpiperidine, 4-[α-(m-trifluoromethylphenyl)-α-hydroxyl]benzylpiperidine, 4-(α-cyclohexyl-α-hydroxy)benzylpiperidine and 4-(α-cyclohexyl)-benzylpiperidine. The foregoing α-hydroxy compounds are prepared from various 1-acetyl-4-benzoylpiperidines wherein the benzoyl group is unsubstituted or is substituted with fluorine in the 4-position, by reaction with Grignard reagents; the 4-bis-diphenylmethylpiperidines are obtained by acid dehydration of the α-hydroxy compounds and catalytic reduction of the resulting 4-bis-phenylmethylene compounds and removal of the 1-acetyl group by hydrolysis under basic conditions. The reaction sequence is as follows:

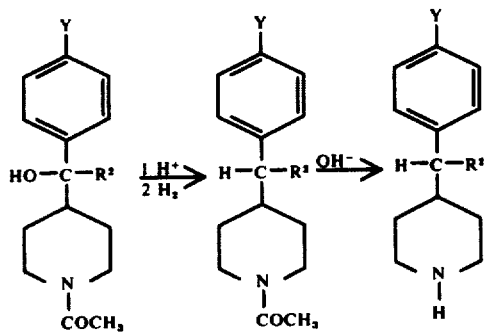

wherein R² and Y have the values previously assigned.

The details of the above procedures are set forth in the following preparations.

PREPARATION 1

4-[α-(p-Fluorophenyl)-α-hydroxy]parafluorobenzyl-piperidine Hydrochloride Hemihydrate To a stirring mixture of 37.7 g. (1.55 moles) of magnesium shavings in about 200 ml. of anhydrous ether (to which a crystal of iodine had been added) was added slowly 268 g. (1.53 moles) of p-fluorobromobenzene in about 500 ml. of anhydrous ether at a rate so as to maintain a controlled reflux. After the addition was complete, the reaction mixture was refluxed for an additional hour and then cooled to about 10° C. A solution of 1-acetyl-4-(p-fluorobenzoyl)piperidine in about 500 ml. of tetrahydrofuran was added dropwise so as to maintain the temperature around 10° C. As the ketone was added, the Grignard complex separated as an oil and then became granular. When the addition was complete, the reaction mixture became semisolid in about 30 minutes. The reaction mixture was added slowly to a saturated solution of ammonium chloride. The solid which separated was collected by filtration, mixed with 6N sodium hydroxide, and extracted with benzene. The extracts were dried over magnesium sulfate, filtered and concentrated under reduced pressure. The solid product was dissolved in benzene and extracted with 3N hydrochloric acid. The acid layer was separated, made basic, and extracted with benzene and chloroform. The combined extracts were dried over magnesium sulfate, filtered, and the filtrate was concentrated under reduced pressure. The residual solid weighed 49 g. (32.3%). The solid was dissolved in isopropanol and an excess of ethereal hydrogen chloride was added. The solvent was removed at reduced pressure, and the residual solid was recrystallized twice from isopropyl ether-isopropanol to give the hydrochloride salt melting at 243°-243.5° C.

Analysis: Calculated for $C_{36}H_{42}Cl_2F_4N_2O_3$: C, 61.98; H, 6.07; N, 4.02; Found: C, 62.02; H, 6.01; N, 3.94.

PREPARATION 2

4-(α-p-Fluorophenyl)-p-fluorobenzylpiperidine Oxalate

To a solution of 26 g. (0.091 mole) of 4-[bis(p-fluorophenyl) methylene]piperidine in 500 ml. of glacial acetic acid was added an excess of palladium-charcoal catalyst. The mixture was shaken and heated in a hydrogen atmosphere for 16 hours. The cooled mixture was filtered, the filtrate was made basic with sodium hydroxide, extracted with benzene and the benzene extracts were dried over anhydrous sodium sulfate and concentrated under vaccum. The white crystalline residue weighed 24.2 g. (84%). The oxalate salt was prepared and melted at 169°-170° C.

Analysis: Calculated for $C_{20}H_{21}F_2NO_4$: C, 63.65; H, 5.61; N, 3.71; Found: C, 63.99; H, 5.75; N, 3.68.

PREPARATION 3

4-[α-(p-fluorophenyl)-α-hydroxybenzylpiperidine

A solution of 33.0 g. (0.103 mole) of 1-acetyl-4-[2-(p-fluorophenyl)-2-hydroxybenzyl]piperidine in 200 ml. of ethanol and 400 ml. of 3N hydrochloric acid was refluxed for 16 hours. The reaction mixture was diluted to about 3 liters with water and extracted with benzene. The combined benzene extracts were washed with water, dried over magnesium sulfate, the mixture filtered, and solvent removed at reduced pressure. A crude solid weighing 20 g. (68%) was obtained and upon recrystallization from benzene-isooctane gave 12.8 g. of solid melting at 140–141° C. The filtrate was reworked to obtain another 1.4 g.

Analysis: Calculated for $C_{18}H_{20}FNO$: C,75.76; H,7.06; N,4.91; Found: C,74.87; H,7.05; N,4.71.

PREPARATION 4

4-(α-p-Fluorophenyl)benzylpiperidine Hydrochloride

To a solution of 30.0 g. (0.112 mole) of α-(p-fluorophenyl) benzylidenepiperidine in 600 ml. of glacial acetic acid was added an excess of palladium charcoal catalyst. The mixture was heated and shaken in 3 atmospheres of hydrogen for several hours. No hydrogen uptake was apparent so the solution was filtered and the filtrate subjected to the same reduction conditions. After 8 hours about 8 lbs. of hydrogen had been taken up. The cooled solution was filtered, made basic with 50% sodium hydroxide solution, diluted to about 3 liters with water and extracted several times with benzene. The combined extracts were dried over anhydrous magnesium sulfate, the dried solution was filtered and the filtrate was concentrated under reduced vacuum. The residual oil weighed 20.0 g. (69%), crystallized upon standing, and melted at 81°–82° C.

Anaylsis: Calculated for $C_{18}H_{21}ClFN$: C,70.69; H,6.92; N,4.58; Found: C,70.69; H,6.93; N,4.52.

PREPARATION 5

4-[α-(3-Trifluoromethylphenyl)-α-hydroxybenzyl-piperidine

A solution of 164.4 g. (0.436 mole) of 1-acetyl-4-[α-(3-trifluoromethylphenyl)-α-hydroxybenzyl]piperidine in 300 ml. of ethanol and 150 ml. of 3N sodium hydroxide was stirred at reflux for 16 hours. The cooled reaction mixture was treated with an excess of water, the aqueous mixture was extracted several times with benzene and the combined extracts were dried over anhydrous sodium sulfate. The mixture was filtered, the filtrate was concentrated under reduced pressure, and the residual crude solid weighed 145 g. Recrystallization of the solid from methanol gave a pale yellow solid which melted at 97°–100° C.

Analysis: Calculated for $C_{19}H_{20}F_3NO$: C,68.05; H,6.01; N,4.18; Found: C,68.03; H,6.01; N,4.04.

PREPARATION 6

4-(α-Cyclohexyl-α-hydroxybenzylpiperidine Hydrochloride Quarterhydrate

A mixture of 25.0 g. (0.0795 mole) of 1-acetyl-4-(α-cyclohexyl-α-hydroxbenzyl)piperidine, 100 ml. of 6N sodium hydroxide and 200 ml. of ethanol was refluxed for 8 hours. The reaction mixture was cooled, diluted to about 800 ml. with water, and extracted with benzene. The extracts were washed with water, dried over anhydrous magnesium sulfate, the mixture filtered and the filtrate concentrated under reduced pressure. The crystalline product obtained weighed 18.1 g. (81%) and melted at 145°–147° C. The product was recrystallized from benzene-ligroin to give 11.0 g. melting at 147°–149° C.

Analysis: Calculated for $C_{72}H_{78}Cl_4N_4O_5$: C,68.99; H,8.84; N,4.47; Found: C,69.08; H,9.14; N,4.50.

PREPARATION 7

4-(α-Cyclohexyl)benzylpiperidine Hydrochloride

A solution of 20.0 g. (0.0785 mole) of 4-(α-cyclohexylbenzylidene)piperidine in 600 ml. of glacial acetic acid was shaken in a hydrogen atmosphere 70° C. for 6 hours using a palladium-charcoal catalyst. The mixture was filtered, the filtrate poured onto 2 liters of cracked ice, the solution made basic with 50% sodium hydroxide and extracted twice with 800 ml. portions of benzene. The combined benzene extracts were dried over anhydrous magensium sulfate, the dried solution filtered, and the filtrate concentrated under reduced pressure. The basic yellow oily residue weighed 18.7 g. (93%) and was converted to the hydrochloride salt. The salt was recrystallized from isopropanol-isopropyl ether and melted at 214°–216° C.

Analysis: Calculated for $C_{18}H_{28}NOCl$: C,73.57; H,9.60; N,4.77; Found: C,73.58; H,9.60; N,4.70.

The novel compounds of the present invention having the foregoing Formula I can be prepared by several methods. Thus, a selection 4-benzylpiperidine of Formula II can be: (a) reacted with a compound R-X (III) wherein X is a reactive halide radical such as chlorine, bromine or iodine, chlorine being a preferred halide; (b) reacted with an active isocyanate compound (IV); and (c) reacted with nitrourea (V), the reaction sequence being:

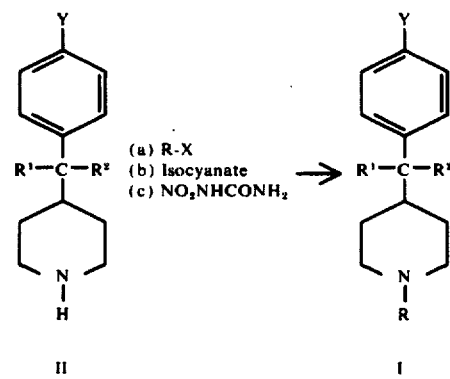

wherein R, R¹, R² and Y are as hereinabove defined.

The compounds of Formula I can also be prepared (d) by reacting a 4-benzyl-1-chlorocarbonyl compound of Formula VI with a selected amine compound R—NH₂ (VII), or (e) by reacting the 1-chlorocarbonyl compound VI, with a selected alcohol R-OH (VIII), the reaction sequence being:

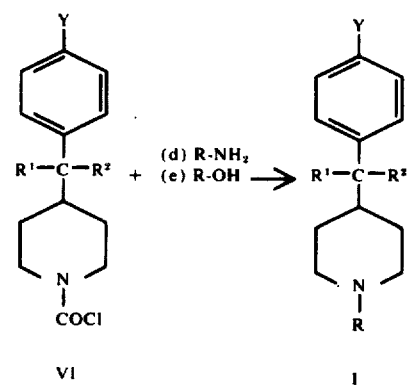

wherein R, R¹, R² and Y are as hereinabove defined.

Additionally, a compound of Formula I wherein R is acetyl can be prepared by (f) reacting a 1-acetyl-4-benzoylpiperidine of Formula IX with a suitable Grignard reactant R²MgX, the reaction sequence being:

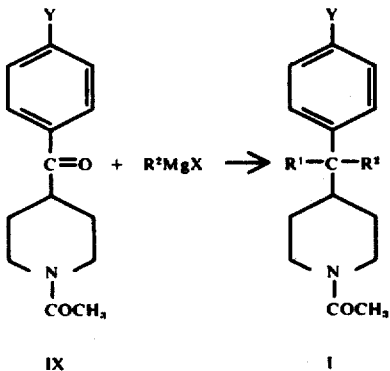

wherein R is acetyl, R¹ is hydroxy, and Y and R² are as defined hereinabove.

The foregoing compounds represented by I wherein R is acetyl, R¹ is hydroxy and Y and R² are as defined hereinabove represent a final product embraced by Formula I and as precursor materials for compounds of Formula II.

The foregoing reaction (a) is carried out in alcoholic solvents such as methanol, ethanol, propanol, 1-butanol, and in a solvent such as dimethylformamide, in the presence of an acid acceptor as, for example, sodium carbonate, potassium carbonate, sodium bicarbonate and the like. The reaction time can vary from about 3 to about 24 hours depending on the reactivity of the halide reactant R-X and the reaction temperature employed can vary from about 80° C. to about 125° C. The foregoing reaction (b) is carried out in a dry inert solvent as, for example, benzene, toluene, xylene and the like and in an ether solvent such as tetrahydrofuran. The reactions are preferably run at room temperature and are generally complete in about two hours. The foregoing reaction (c) is carried out in a lower alkanol solvent such as ethanol, 1-butanol, and the like or in a mixed alkanol-halogenated aliphatic solvent such as ethanol-chloroform. The reactions are preferably run at the boiling point of the selected solvent or solvent system and for a reaction period of from about one hour to about 3 hours. The foregoing reactions (d) and (e) are run in an inert hydrocarbon solvent such as benzene, toluene or the like or in a ketone solvent such as methyl ethyl ketone in the presence of a base such an an alkali carbonate or a teritiary amine such as triethylamine. The reaction time can vary from about 2 hours to about 15 hours at the reflux temperature of the solvent employed. Reaction (f) is the known Grignard reaction and employs reaction conditions generally applicable to Grignard reaction.

The details of the foregoing procedures are exemplified in Examples 1–9. Examples 10–38 summarized in Tables I and II are prepared using the procedures described in Examples 1–9.

EXAMPLE 1

1-[3-(p-Acetyl-o-methoxyphenoxy)propyl]-4-(α-cyclohexyl) benzylpiperidine Oxalate Hemihydrate A mixture of 5.2 g. (0.02 mole) of 4-(α-cyclohexylbenzyl) piperidine, 4.9 g. (0.02 mole) of 3-(p-acetyl-o-methoxyphenoxy) propyl chloride and 1.7 g. (0.02 mole) of sodium bicarbonate and 100 ml. of dimethylformamide was stirred at 100° C. for 4 hours. The cooled reaction mixture was filtered, the dimethylformamide was removed under reduced pressure and the residual material was dissolved in benzene and placed on a magnesium silicate column. Elution using an acetone-benzene gradient gave 7.0 g. (74.5%) of product. The oxalate salt was prepared and melted at 155°-160° C. after recrystallization from isopropanol.

Analysis: Calculated for $C_{64}H_{88}N_2O_{15}$: C,68.31; H,7.88; N,2.49; Found: C,68.60; H,7.78; N,2.42.

EXAMPLE 2

1-[3-(p-Fluorobenzoyl)propyl]-4-(α-cyclohexyl-α-hydroxy) benzylpiperidine Hydrochloride A mixture of 4.0 g. (0.0147 mole) of 4-(α-cyclohexyl-α-hydroxybenzyl)piperidine, 3.9 g. (0.016 mole) of 2-(3-chloropropyl)-2-(p-fluorophenyl)dioxolane, 2.7 g. (0.032 mole) of sodium bicarbonate and 100 ml. of 1-butanol was refluxed for 20 hours. The mixture was filtered, the filtrate concentrated under reduced pressure, and the residual oil was stirred overnight in a mixture of 100 ml. of ethanol and 50 ml. of 6N hydrochloric acid. The reaction mixture was diluted to 600 ml. with water and made basic, the mixture extracted with benzene and the combined extracts were dried over anhydrous magnesium sulfate. The mixture was filtered and the filtrate was concentrated under reduced pressure to give 4.9 g. (64.5%) of crude product. The oil was dissolved in ether and an excess of ethereal hydrogen chloride was added. The resulting hydrochloride salt was recrystallized from methanol-isopropyl ether to give 2.7 g. of product melting at 274°-275° C.

Analysis: Calculated for $C_{28}H_{37}ClFNO_2$: C,70.94; H,7.87; N,2.96; Found: C,70.99; H,7.88; N,2.89.

EXAMPLE 3

1-{2-[4-(p-Fluorobenzoyl)piperidino]ethyl}-4-(α-p-fluorophenyl)-p-fluorobenzylpiperidine Dihydrochloride A mixture of 6.0 g. (0.022 mole) of 1-(2-chloroethyl)-4-(p-fluorobenzoyl)piperidine, 6.4g. (0.022 mole) of 4-[bis(p-fluorophenyl)methyl]piperidine and 5.5g. (0.04 mole) of potassium carbonate in 100 ml. of 1-butanol was stirred at gentle reflux for 21 hours. An excess of water was added and the mixture was extracted with benzene. The combined extracts were dried over anhydrous sodium sulfate, the mixture was filtered and the filtrate was concentrated under vacuum. The residue wad dissolved in anhydrous ether and an excess of ethereal hydrogen chloride was added. The hydrochloride salt weighed 4.1 g. (31%) and melted at 275° C. (dec.). The salt was recrystallized from isopropanol-methanol-ether.

Analysis: Calculated for $C_{32}H_{27}Cl_2F_3N_2O$: C,64.75; H,6.28; N,4.72; Found: C,64.18; H,6.31; N,4.62.

EXAMPLE 4

N,N-Dimethyl-4-(α-p-fluorophenyl)-p-fluorobenzylpiperidine-1-carboxamide

To a stirring mixture of 5.75 g. (0.02 mole) of 4-[bis(p-fluorophenyl)methyl]piperidine and 10.0 g. of potassium carbonate in 100 ml. of dry benzene was slowly added 2.15 g. (0.02 mole) of N,N-dimethylcarbamoyl chloride. The reaction mixture was stirred at room temperature for 3 hours and then refluxed for one hour. The mixture was filtered and the benzene was removed at reduced pressure. The residue which crystallized upon standing was dissolved in benzene and placed on a magnesium silicate column. Elution with an acetone-benzene gradient gave the product melting at 104.5°–106° C.

Analysis: Calculated for $C_{21}H_{24}N_2OF_2$: C,70.37; H,6.75; N,7.82; Found: C,70.76; H,6.80; N,7.77.

EXAMPLE 5

4-(α-Phenyl)benzylpiperidine-1-carboxanilide

To a stirring solution of 5.0 g. (0.02 mole) of 4-(α-phenylbenzyl)piperidine in 100 ml. of dry benzene was added 2.4 g. (0.02 mole) of phenyl isocyanate in 25 ml. of dry benzene. The mixture was stirred for 2 hours after the addition was complete and the product separated from solution as a solid. The solid was collected to give 6.6 g. (90.5%) of product. The solid was recrystallized from benzene and melted at 243°–245° C.

Analysis: Calculated for $C_{25}H_{26}N_2O$: C,81.05; H,7.07; N,7.56; Found: C,80.74; H,7.05; N,7.38.

EXAMPLE 6

4-[α-(p-Fluorophenyl)-α-hydroxy]-p-fluorobenzyl-piperidine-1-(3-trifluoromethyl)carboxanilide To a solution of 5.0 g. (0.016 mole) of 4-[bis(p-fluorophenyl)hydroxymethyl]piperidine in 75 ml. of dry benzene was added dropwise a solution of 3.2 g. (0.017 mole) of m-trifluoromethylphenylisocyanate in 25 ml. of dry benzene. After the addition was complete, the reaction mixture was stirred at room temperature for 2 hours. The mixture was concentrated under reduced pressure. The brown residue was dissolved in benzene and placed on a magnesium silicate column. Elution using a benzene-acetone gradient gave 2.7 g. (33%) of product. Recrystallization from benzene-isooctane gave 2.3 g. of product melting at 151.5°–152.5° C.

Analysis: Calculated for $C_{26}H_{23}F_5N_2O_2$: C,63.67; H,4.73; N,5.71; Found: C,63.86; H,4.74; N,5.67.

EXAMPLE 7

1-[2-(2-Pyridyl)ethyl]-4-(α-p-fluorophenyl)-p-fluoro-benzyl-piperidine-1-carboxamide A mixture of 4.0 g. (0.0155 mole) of 4-[bis(p-fluorophenyl) methyl]piperidinecarbonyl chloride, 1.4 g. (0.0155 mole) of 2-(2-aminoethyl)pyridine and 1.5 g. (0.0143 mole) of triethylamine in 100 ml. of ethyl methyl ketone was stirred for 15 minutes and then refluxed for two hours. The mixture was cooled to room temperature, filtered to remove the triethylamine hydrochloride, the filtrate was concentrated under reduced pressure, and the residue was dissolved in benzene and placed on a magnesium silicate column. The produce which was eluted from the column using an acetone-benzene gradient crystallized in isopropyl ether. The solid melted at 112°–120° C.

Analysis: Calculated for $C_{26}H_{27}N_3OF_2$: C,71.71; H,6.25; N,9.65; Found: C,71.50; H,6.27; N,9.44.

EXAMPLE 8

4-(α-p-Fluorophenyl)-p-fluorobenzylpiperidine-1-carboxamide

A mixture of 4.75 g. (0.0165 mole) of 4-[bis(p-fluorophenyl) methyl]piperidine and 1.8 g. (0.0165 mole) of nitrourea in 50 ml. of absolute ethanol was warmed on a steam bath until evolution of gas ceased. The mixture was refluxed for one hour. After filtering the mixture the solvent was removed under reduced pressure, the residual solid was dissolved in 50 ml. of chloroform, filtered and the chloroform was removed under reduced pressure. The gummy residue was triturated in isopropyl ether and 5.5 g. (99%) of solid product was collected by filtration. The solid was recrystallized from benzene-isopropyl ether to give 2.8 g. of product melting at 204°–205° C.

Analysis: Calculated for $C_{19}H_{20}F_2N_2O$: C,69.08; H,6.10; N,8.48; Found: C,69.29; H,6.26; N,8.19.

EXAMPLE 9

1-Acetyl-4-(α-cyclohexyl-α-hydroxy)benzylpiperidine

Under anhydrous conditions, 282.0 g. (1.72 moles) of cyclohexyl bromide in 500 ml. of anhydrous ether was added dropwise to a stirring mixture of 39.7 g. (1.72 moles) of magnesium turnings in 300 ml. of anhydrous ether at a rate so as to maintain a moderate reflux. After the addition was complete, the reaction mixture was refluxed for one-half hour and cooled to 10° C. A solution of 143.5 g. (0.575 mole) of 1-acetyl-4-benzoylpiperidine in 600 ml. of dry tetrahydrofuran was added dropwise to the reaction mixture while maintaining the temperature at 10° C. After the addition was complete, the stirring reaction mixture was allowed to come to room temperature and then poured onto about 1 kg. of ice and 159 g. (3 moles) of ammonium chloride. The ether layer was separated, washed with water, and dried over anhydrous magnesium sulfate. The ether mixture was filtered and the filtrate was concentrated under reduced pressure to give 168.6 g. of crude product which crystallizd upon trituration in isopropyl ether. The solid product collected by filtration weighed 136.0 g. (75%), and upon recrystallization from ethyl acetate gave the product melting at 153°–155° C.

Analysis: Calculated for $C_{20}H_{29}NO_2$: C,76.15; H,9.27; N,4.44; Found: C,76.23; H,9.41; N,4.38.

The physical constant of some representative 1-substituted-4-benzylpiperidines made by the procedures disclosed hereinabove and as set forth in detail in Examples 1–9 are shown in Table I and Table II.

Table I

EXAMPLES 10 TO 38

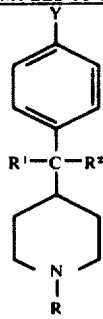

| Ex. | R | R¹ | R² | Y | M.P. °C. | Salt |
|---|---|---|---|---|---|---|
| 10 | H₂NCOCH₂CH₂— | H | p-FC₆H₄— | F | 212-3 | HCl |
| 11 | p-CH₃CO-o-CH₃OC₆H₃OC₃H₆— | H | C₆H₅— | H | 149-55 | C₂H₂O₄ |
| 12 | " | OH | p-FC₆H₄— | F | 141.5-3 | — |
| 13 | " | H | p-FC₆H₄— | F | 164.5-6 | C₂H₂O₄ |
| 14 | " | OH | C₆H₅— | F | 147-8 | — |
| 15 | " | OH | C₆H₅— | H | 174-6 | C₂H₂O₄ |
| 16 | " | OH | m-CF₃C₆H₄— | H | 95 | HCl½ H₂O |
| 17 | " | OH | C₆H₁₁— | H | 152-5 | HCl |
| 18 | p-FC₆H₄COC₃H₆— | OH | p-FC₆H₄— | F | 156-8 | C₂H₂O₄ |
| 19 | " | H | p-FC₆H₄— | F | — | — |
| 20 | " | OH | C₆H₅— | F | 142-4 | C₂H₂O₄ |
| 21 | " | H | C₆H₅— | F | 89-90 | — |
| 22 | " | OH | m-CF₃C₆H₄— | H | 150-3 | ½H₂O |
| 23 | " | H | C₆H₁₁— | H | 108-9 | C₂H₂O₄ |
| 24 | C₆H₅NHCO— | H | C₆H₁₁— | H | 190.5-2 | — |
| 25 | " | OH | C₆H₁₁— | H | 218-9 | ½H₂O |
| 26 | " | OH | m-CF₃C₆H₄— | H | 62-4.5 | — |
| 27 | " | OH | C₆H₅— | H | 214-15 | — |
| 28 | " | H | C₆H₅— | F | 227-7.5 | — |
| 29 | " | OH | p-FC₆H₄— | F | 171-3 | — |
| 30 | m-CF₃C₆H₄NHCO— | OH | p-FC₆H₄— | F | 151.5-2.5 | — |
| 31 | CH₃NHCO— | H | p-FC₆H₄— | F | 94-8 | — |
| 32 | o-CH₃OC₆H₄OCH₂CHOHCH₂OC(O)—H | p-FC₆H₄— | F | — | — | |
| 33 | (CH₃)₂NC₃H₆NHCO— | H | p-FC₆H₄— | F | — | HCl½ H₂O |
| 34 | CH₃CH₂OCH₂CH₂NC₃H₄NHCO— | H | p-FC₆H₄— | F | — | — |
| 35 | CH₃CO— | OH | C₆H₅— | H | 204.5-5 | — |
| 36 | " | OH | C₆H₅— | F | 172.5-4 | — |
| 37 | " | OH | p-FC₆H₄— | F | 195.5-8 | — |
| 38 | H₂NCO— | OH | p-FC₆H₄— | F | 102-5 | — |

Note: C₂H₂O₄ is oxalate; HCl is hydrochloride

TABLE II

ANALYTICAL DATA ON EXAMPLES 10 TO 38

| Example | Empirical Formula | Calculated | | | Found | | |
|---|---|---|---|---|---|---|---|
| | | C | H | N | C | H | N |
| 10 | C₂₁H₂₃ClF₂N₂O | 63.87 | 6.38 | 7.09 | 63.85 | 6.35 | 6.98 |
| 11 | C₃₂H₃₇NO₇ | 70.18 | 6.81 | 2.56 | 70.00 | 6.76 | 2.56 |
| 12 | C₃₀H₃₃F₂NO₄ | 70.71 | 6.53 | 2.75 | 70.49 | 6.58 | 2.59 |
| 13 | C₃₂H₃₅F₂NO₇ | 65.86 | 6.05 | 2.40 | 66.11 | 6.13 | 2.39 |
| 14 | C₃₀H₃₄FNO₄ | 73.30 | 6.97 | 2.85 | 73.15 | 7.05 | 2.77 |
| 15 | C₃₂H₃₇NO₈ | 68.19 | 6.62 | 2.49 | 68.34 | 6.75 | 2.42 |
| 16 | C₆₂H₇₂Cl₂F₆N₂O₉ | 63.42 | 6.18 | 2.39 | 63.68 | 6.03 | 2.33 |
| 17 | C₃₀H₄₂ClNO₄ | 69.82 | 8.20 | 2.71 | 69.50 | 8.31 | 2.62 |
| 18 | C₃₀H₃₀F₃NO₆ | 64.63 | 5.42 | 2.51 | 64.28 | 5.51 | 2.40 |
| 19 | C₂₈H₂₈F₃NO | 74.48 | 6.25 | 3.10 | 74.13 | 6.38 | 2.90 |
| 20 | C₃₀H₃₁F₂NO₆ | 66.78 | 5.79 | 2.60 | 66.65 | 5.87 | 2.56 |
| 21 | C₂₈H₂₉F₂NO | 77.57 | 6.74 | 3.23 | 77.36 | 6.77 | 3.15 |
| 22 | C₅₈H₆₀F₈N₂O₅ | 68.49 | 5.95 | 2.75 | 68.79 | 5.90 | 2.69 |
| 23 | C₃₀H₃₈FNO₅ | 70.43 | 7.49 | 2.74 | 70.29 | 7.45 | 2.69 |
| 24 | C₂₅H₃₂N₂O | 79.75 | 8.57 | 7.44 | 80.05 | 8.64 | 7.48 |
| 25 | C₅₀H₆₆N₄O₅ | 75.86 | 7.93 | 6.68 | 75.62 | 8.11 | 6.87 |
| 26 | C₂₆H₂₅F₃N₂O₂ | 68.71 | 5.54 | 6.16 | 68.89 | 5.66 | 6.12 |
| 27 | C₂₅H₂₆N₂O₂ | 77.69 | 6.78 | 7.25 | 77.68 | 6.78 | 7.15 |
| 28 | C₂₅H₂₅FN₂O | 77.29 | 6.49 | 7.21 | 77.45 | 6.51 | 7.15 |
| 29 | C₂₅H₂₄F₂N₂O₂ | 71.08 | 5.73 | 6.63 | 71.05 | 5.78 | 6.62 |
| 30 | C₂₆H₂₃F₅N₂O₂ | 63.67 | 4.73 | 5.71 | 63.86 | 4.74 | 5.67 |
| 31 | C₂₀H₂₂F₂N₂O | 69.75 | 6.44 | 8.13 | 69.70 | 6.47 | 7.86 |
| 32 | C₂₈H₃₁F₂NO₅ | 68.09 | 6.11 | 2.74 | 67.84 | 6.26 | 2.71 |
| 33 | C₄₈H₆₆Cl₂F₄N₆O₃ | 62.53 | 7.22 | 9.12 | 62.72 | 7.24 | 8.78 |
| 34 | C₂₅H₃₁F₂N₃O₂ | 67.70 | 7.05 | 9.47 | 68.03 | 7.22 | 9.14 |
| 35 | C₂₀H₂₃NO₂ | 77.64 | 7.49 | 4.53 | 77.50 | 7.55 | 4.43 |
| 36 | C₂₀H₂₂FNO | 73.37 | 6.77 | 4.29 | 73.27 | 6.84 | 4.04 |
| 37 | C₂₀H₂₁F₂NO₂ | 69.55 | 6.13 | 4.06 | 69.61 | 6.14 | 4.03 |
| 38 | C₁₉H₂₀F₂N₂O₂ | 65.89 | 5.82 | 8.09 | 65.63 | 5.86 | 7.73 |

The compounds of the invention are generally characterized by the pharmacological activity hereinbefore stated, making them useful in counteracting certain physiological abnormalities in a living animal body. Effective quantities of the pharmacologically active compounds of the invention may be administered to a living animal body in any one of various ways, for example, orally as in capsules or tablets, parenterally in the form of sterile solutions, suspensions, and in some cases intravenously in the form of sterile solutions. Other modes of administration are cutaneous, subcutaneous, intramuscular and intraperitoneal.

Pharmaceutical formulations are usually prepared from a predetermined quantity of one or more of the compounds of the invention, preferably in solid form. Such formulations may take the form of powders, elixirs, solutions, pills, capsules, or tablets, with or without, but preferably with, any one of a large variety of pharmaceutically acceptable vehicles or carriers. When in admixture with a pharmaceutical vehicle or carrier, the active ingredient usually comprises from about 0.01 to about 75%, normally from about 0.05 to about 25%, by weight of the composition. Carriers such as starch, sugar, talc, commonly used synthetic and natural gums, water, and the like, may be used in such formulations. Binders such as gelatin and lubricants such as sodium stearate may be used to form tablets. Disintegrating agents such as sodium bicarbonate may also be included in tablets.

Although relatively small quantities of the active materials of the invention, even as low as 0.1 mg., may be used in cases of administration to subjects having a relatively low body weight, unit dosages are usually 5 mg. or above, and preferably 25, 50, or 100 mg. or even higher, depending, of course, upon the subject treated and the particular result desired. The usual broader ranges appear to be 1-200 mg. per unit dose. The active agents of the invention may be combined for administration with other pharmacologically active agents, such as buffers, antacids, or the like, and the proportion of the active agent or agents in the compositions may be varied widely. It is only necessary that the active ingredient of the invention constitute an effective amount, i.e., such that a suitable effective dosage will be obtained consistent with the dosage form employed. Obviously, several unit dosage forms may be administered at about the same time. The exact individual doses, as well as daily dosage, in a particular case will, of course, be determined according to well-established principles under the direction of a physician or a veterinarian.

It is to be understood that the invention is not to be limited to the exact details of operation or exact compounds, compositions, or procedures shown and described, as obvious modifications and equivalents will be apparent to one skilled in the art, and the invention is therefore to be limited only by the scope of the appended claims.

We claim:
1. A pharmaceutical composition useful for its sedative and tranquilizing effects comprising
a. 1 to 200 mg. of a compound selected from the group consisting of a 1-substituted-4-benzylpiperidine of the formula

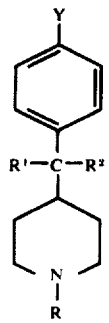

wherein;
R is selected from the group consisting of p-fluorobenzoylpropyl, p-acetyl-o-methoxyphenoxypropyl, carbamoyl, N-lower-alkylcarbamoyl, N,N-dilower-alkylcarbamoyl, N-phenylcarbamoyl, N-(m-trifluoromethylphenyl)carbamoyl, N-(ω-morpholino)lower-alkylcarbamoyl, N-[ω-(2-pyridyl)-lower-alkyl]carbamoyl, 2-hydroxy-3-(o-methoxyphenoxy)propyloxycarbonyl, 2-carbamoylethyl or 4-(p-fluorobenzoyl)piperidinoethyl, $R^1$ is selected from the group consisting of hydrogen or hydroxy, $R^2$ is selected from the group consisting of phenyl, p-fluorophenyl, m-trifluoromethylphenyl or cyclohexyl, Y is selected from the group consisting of hydrogen or fluorine, with the proviso that when Y is hydrogen and $R^2$ is phenyl, R is other than p-fluorobenzoylpropyl, and a pharmaceutically acceptable acid addition salt of a basic compound thereof, and b. a pharmaceutically acceptable carrier therefor.

2. A composition of claim 1 wherein $R^1$ represents hydroxy.

3. A composition of claim 2 wherein the compound is 1-[3-(p-acetyl-o-methoxyphenoxy)propyl]-4-(α-p-fluorophenyl-α-hydroxy)-p-fluorobenzylpiperidine.

4. A composition of claim 2 wherein the compound is 1-[3-(p-acetyl-o-methoxyphenoxy)propyl]-4-(α-p-fluorophenyl-α-hydroxy)benzylpiperidine.

5. A composition of claim 2 wherein the compound is 1-[3-(p-fluorobenzoyl)propyl]-4-(α-p-fluorophenyl-α-hydroxy)-p-fluorobenzylpiperidine.

6. A composition of claim 2 wherein the compound is 1-[3-(p-fluorobenzoyl)propyl]-4-(α-m-trifluoromethylphenyl-α-hydroxy) benzylpiperidine.

7. A composition of claim 2 wherein the compound is N-phenyl-4-(α-p-fluorophenyl-α-hydroxy)-p-fluorobenzylpiperidine-1-carboxamide.

8. A composition of claim 2 wherein the compound is N-phenyl-4-(α-cyclohexyl-α-hydroxy)benzylpiperidine-1-carboxamide.

9. A composition of claim 2 wherein the compound is 1-acetyl-4-(α-p-fluorophenyl-α-hydroxy)benzylpiperidine.

10. A composition of claim 1 wherein $R^1$ represents hydrogen.

11. A composition of claim 10 wherein the compound is 1-[3-(p-fluorobenzoyl)propyl]-4-(α-p-fluorophenyl)-p-fluorobenzylpiperidine.

12. A composition of claim 10 wherein the compound is 1-[3-(p-acetyl-o-methoxyphenoxy)propyl]-4-(α-p-fluorophenyl)-p-fluorobenzylpiperidine.

13. A composition of claim 10 wherein the compound is N-(2-morpholinoethyl)-4-(α-p-fluorophenyl)-p-fluorobenzylpiperidine-1-carboxamide.

14. A composition of claim 10 wherein the compound is N-[2-(2-pyridyl)ethyl]-4-(α-p-fluorophenyl)-p-fluorobenzylpiperidine-1-carboxamide.

15. A composition of claim 10 wherein the compound is 1-[3-(p-fluorobenzoyl)propyl]-4-(α-cyclohexyl)benzylpiperidine.

16. A composition of claim 10 wherein the compound is 1-[3-(p-acetyl-o-methoxyphenoxy)propyl]-4-(α-phenyl)benzylpiperidine.

17. A composition of claim 10 wherein the compound is 1-(2-carbamoylethyl)-4-(α-p-fluorophenyl)-p-fluorobenzylpiperidine.

18. A method of sedating or tranquilizing a living animal which comprises administering to said animal a compound selected from the group consisting of a 1-substituted-4-benzylpiperidine of the formula

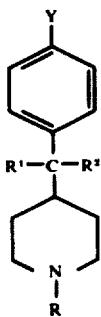

wherein;
R is selected from the group consisting of, p-fluorobenzoylpropyl, p-acetyl-o-methoxyphenoxypropyl, carbamoyl, N-loweralkylcarbamoyl, N,N-dilower-alkylcarbamoyl, N-phenyl-carbamoyl, N-(m-trifluoromethylphenyl)carbamoyl, N-(ω-morpholino) lower-alkylcarbamoyl, N-[ω-(2-pyridyl)-lower-alkyl]carbamoyl, 2-hydroxy-3-(o-methoxyphenoxy)propyloxycarbonyl, 2-carbamoylethyl or 4-(p-fluorobenzoyl)piperidinoethyl,
$R^1$ is selected from the group consisting of hydrogen or hydroxy,
$R^2$ is selected from the group consisting of phenyl, p-fluorophenyl, m-trifluoromethylphenyl or cyclohexyl,
Y is selected from the group consisting of hydrogen or fluorine, with the proviso that when Y is hydrogen and $R^2$ is phenyl, R is other than p-fluorobenzoylpropyl, and a pharmaceutically acceptable acid addition salt of a basic compound thereof.

19. A method of claim 18 wherein $R^1$ represents hydroxy.

20. A method of claim 19 wherein the compound is 1-[3-(p-acetyl-o-methoxyphenoxy)propyl]-4-(α-p-fluorophenyl-α-hydroxy)-p-fluorobenzylpiperidine.

21. A method of claim 19 wherein the compound is 1-[3-(p-acetyl-o-methoxyphenoxy)propyl]-4-(α-p-fluorophenyl-α-hydroxy)benzylpiperidine.

22. A method of claim 19 wherein the compound is 1-[3-(p-fluorobenzoyl)propyl]-4-(α-p-fluorophenyl-α-hydroxy)-p-fluorobenzylpiperidine.

23. A method of claim 19 wherein the compound is 1-[3-(p-fluorobenzoyl)propyl]-4-(α-m-trifluoromethylphenyl-α-hydroxy) benzylpiperidine.

24. A method of claim 19 wherein the compound is N-phenyl-4-(α-p-fluorophenyl-α-hydroxy)-p-fluorobenzylpiperidine-1-carboxamide.

25. A method of claim 19 wherein the compound is N-phenyl-4-(α-cyclohexyl-α-hydroxy)benzylpiperidine-1-carboxamide.

26. A method of claim 19 wherein the compound is 1-acetyl-4-(α-p-fluorophenyl-α-hydroxy)benzylpiperidine.

27. A method of claim 18 wherein $R^1$ represents hydrogen.

28. A method of claim 27 wherein the compound is 1-[3-(p-fluorobenzoyl)propyl]-4-(α-p-fluorophenyl)-p-fluorobenzylpiperidine.

29. A method of claim 27 wherein the compound is 1-[3-(p-acetyl-o-methoxyphenoxy)propyl]-4-(α-p-fluorophenyl)-p-fluorobenzylpiperidine.

30. A method of claim 27 wherein the compound is N-(2-morpholinoethyl)-4-(α-p-fluorophenyl)-p-fluorobenzylpiperidine-1-carboxamide.

31. A method of claim 27 wherein the compound is N-[2-(2-pyridyl)ethyl]-4-(α-p-fluorophenyl)-p-fluorobenzylpiperidine-1-carboxamide.

32. A method of claim 27 wherein the compound is 1-[3-(p-fluorobenzoyl)propyl]-4-(α-cyclohexyl)benzylpiperidine.

33. A method of claim 27 wherein the compound is 1-[3-(p-acetyl-o-methoxyphenoxy)propyl]-4-(α-phenyl)benzylpiperidine.

34. A method of claim 27 wherein the compound is 1-(2-carbamoylethyl)-4-(α-p-fluorophenyl)-p-fluorobenzylpiperidine.

* * * * *